US005584854A

United States Patent [19]

Minarik

[11] Patent Number: 5,584,854

[45] Date of Patent: Dec. 17, 1996

[54] ACUPRESSURE DEVICE

[76] Inventor: Richard Minarik, 61-61 Woodhaven Blvd., Rego Park, Queens, New York City, N.Y. 11374

[21] Appl. No.: 512,288

[22] Filed: Aug. 8, 1995

[51] Int. Cl.$^6$ .................................................... A61B 17/00

[52] U.S. Cl. ........................... 606/201; 606/203; 606/204

[58] Field of Search .................................... 606/201, 203, 606/204, 204.15, 204.25, 130, 54, 56

[56] References Cited

U.S. PATENT DOCUMENTS

| | | | |
|---|---|---|---|
| 737,473 | 8/1903 | Porter . | |
| 1,281,653 | 10/1918 | Plummer . | |
| 1,299,860 | 4/1919 | Plummer . | |
| 2,711,167 | 6/1952 | Rickard . | |
| 3,884,240 | 5/1975 | Gilman | 128/325 |
| 4,384,574 | 5/1983 | Wong | 128/133 |
| 4,479,495 | 10/1984 | Isaacson | 128/327 |
| 5,094,227 | 3/1992 | Eglauf et al. | 128/60 |
| 5,423,853 | 6/1995 | Lasvignes | 606/204 |

*Primary Examiner*—Michael Powell Buiz
*Assistant Examiner*—Mark S. Leonardo
*Attorney, Agent, or Firm*—Robert W. J. Usher

[57] ABSTRACT

Acupressure clamps include a U-shape band having opposite end portions respectively provided with a pressure applying screw and a spherical counterabutment. The end portions can be parallel with a line of action of the screw extending through the protuberance for application of pressure to precisely opposite portions of a foot or, the end portions can diverge for simultaneous application of pressures along non aligned axes at two locations on a back of a hand. Another device for the leg below the knee or the sole of the foot has a body engaging, arcuate plate carrying a pressure screw and mounted on a fastening strap. A device for the big toe is a socket with a pressure screw and a device for smaller toes is a clip.

13 Claims, 2 Drawing Sheets

FIG. 1
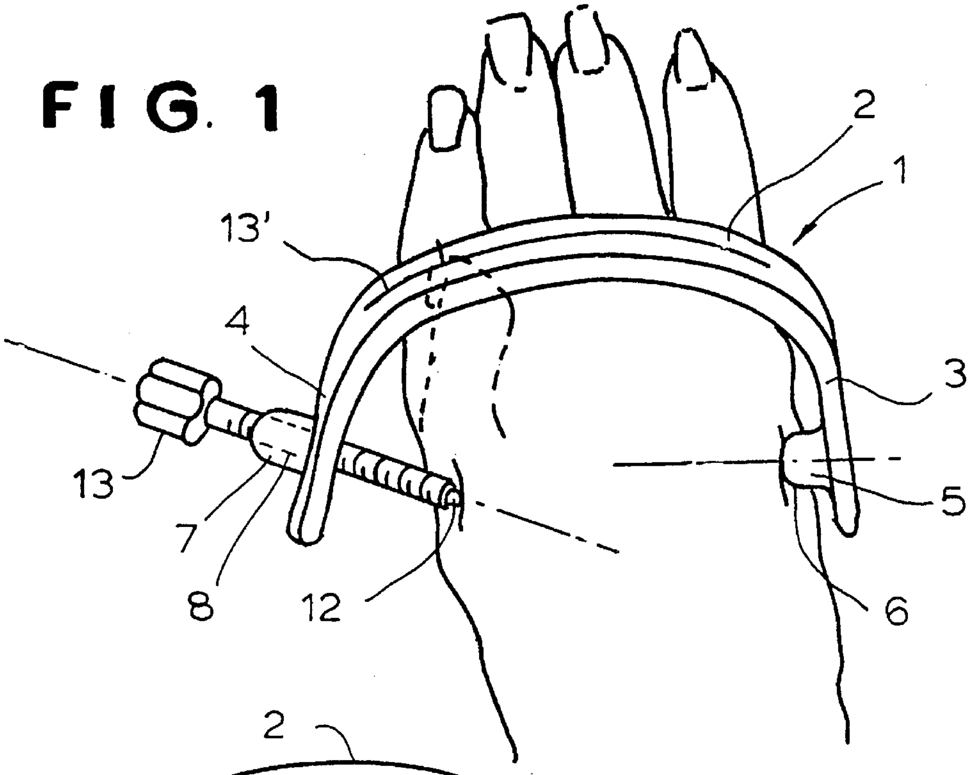
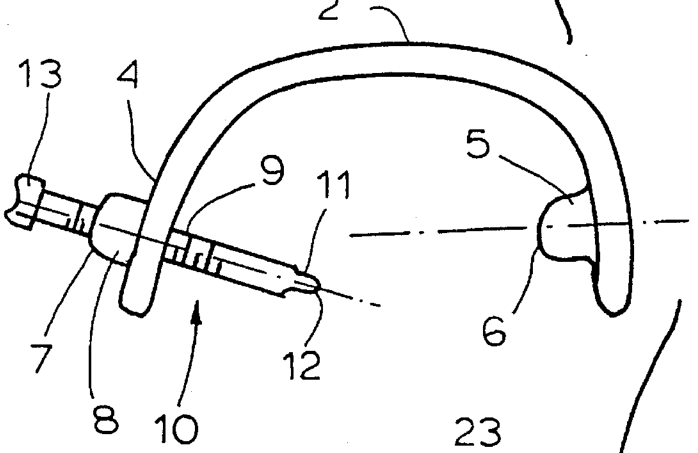
FIG. 2
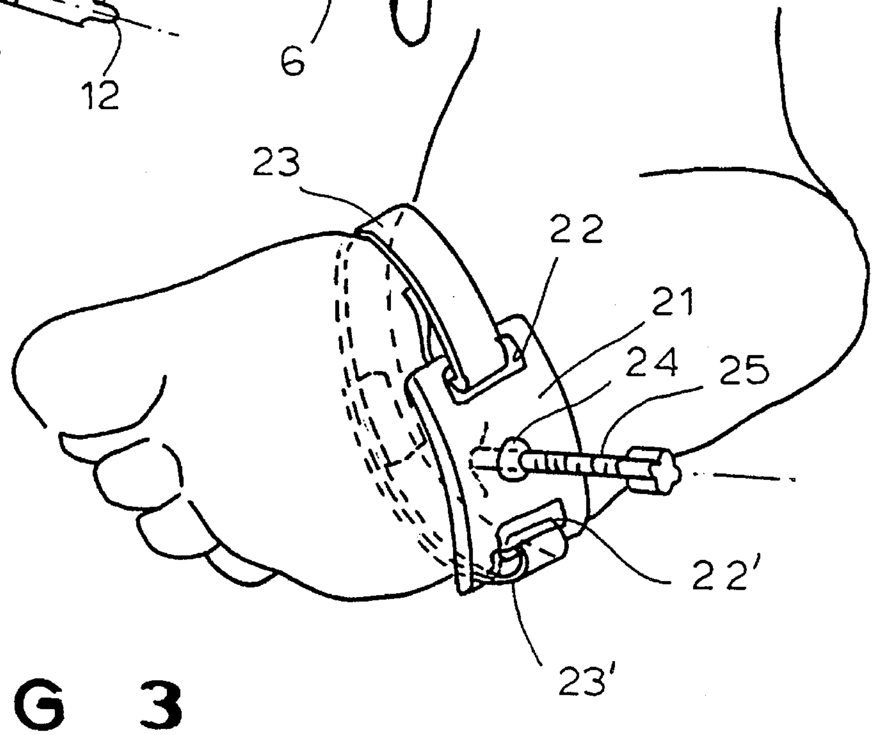
FIG 3

ACUPRESSURE DEVICE

FIELD OF THE INVENTION

The invention relates to medical devices for the application of pressure to appendages of the human body for the treatment of discomfort, in particular to relieve pain.

BACKGROUND OF THE INVENTION

It has been recognized for many years that acupressure, which is the application of non-invasive stimulative pressure at discrete points of the human body, particularly at recognized acupuncture points, can relieve pain or discomfort in other locations of the body. It is believed that the relief is obtained by a mechanism essentially the same as that operative in acupuncture in that the application of pressure causes the nerves to stimulate the pituitary to release pain killing and relaxing hormones known as endorphins which can also create a euphoric state of relaxation, reported to relieve stiffness, bodily tensions, nervousness, hyperactivity, depressions and insomnia.

In order to avoid the expense of the presence of a practitioner to administer the treatment, various devices have been proposed to apply a sustained pressure to selected points on the human body.

In particular, reference is made to U.S. Pat. 4,479,495 issued to Isaacson in 1984 and U.S. Pat. 5,094,227 issued to Eglauf in 1992, the disclosures of which are incorporated herein for more detailed information concerning the theory and practice of the acupressure technique.

Although, the above-mentioned patents, together with U.S. Pat. 5,423,853 issued to Lasvignes in 1995 teach devices which may possibly be suitable for particular applications, various of such devices may be relatively complex and expensive to manufacture, of restricted application or relatively difficult for an individual user to apply with the required precision to selected acupressure points and to adjust in situ to obtain the desired pressure.

SUMMARY OF THE INVENTION

It is an object of the invention to provide one or more devices that an individual user can apply with the required precision to selected acupressure points and adjust in situ to obtain a desired pressure.

It is a further object of the invention to provide such devices which can be mass produced at high volume and at low unit cost for wide availability.

According to one aspect of the invention, there is provided a set of pressure applying devices which are shaped and configured for mounting on various different parts of the body to apply pressure to selected points thereof.

One type of clamping device may comprise a unitary, generally U-shape band having opposite end portions connected by a bight, screw mounting means on one end portion and an inward extending, counter-abutting protuberance having a spherical tip formed on an inner side of an opposite end portion; and, a tightening screw having a pressure applying end terminating in a smooth, spherical pressing tip substantially smaller than the protuberance and an opposite, adjustment end, having a fingerpiece, the tightening screw being mounted by said screw mounting means with the tip extending inward and the fingerpiece accessible outside the end portion.

This construction enables the clamping device to be mounted on a user's body part engaged between the protuberance and the pressing tip and the fingerpiece manually rotated by the user to adjust precisely applied pressure while maintaining aligned engagement of the pressing tip with a selected acupressure point with the protuberance providing a stabilizing counterabutment. The larger spherical tip of the counterabutment affords force distribution to avoid discomfort while ensuring stability of location for tightening.

In one embodiment, the free ends of the band may extend in substantially parallel relation with a line of action or screw axis passing directly through the counter-abutting protuberance thereby applying pressure to precisely opposite portions of the body portion embraced thereby or, may be inclined at an acute angle thereto for simultaneous application of pressures along non aligned axes at two spaced apart Acupressure points on a body part such as the back of the hand. The latter version is particularly suited for application to the back of the hand with the screw inclined to the surface so as to be capable of applying pressure to a point adjacent or behind a boney mass such as the Ho Ku point.

The band may be is molded in one piece from plastic, and the screw mounting means formed by a land integrally molded on an outside of the one end portion. This permits an extremely inexpensive construction while the provision of the land enables the band to remain desirably thin and light, also minimizing the amount of material required for manufacture.

Another device for application to selected acupressure points on the sole of the foot and the leg, immediately below the knee, comprises a unitary mounting plate of arcuate section formed at a central location with screw mounting means and with strap anchoring portions at opposite circumferential ends; fastening strap means attached to the anchoring portions; and, a tightening screw having a pressure applying end terminating in a small, spherical pressing tip and an opposite, adjustment end, having a fingerpiece. The screw mounting means mounts the tightening screw extending through the center of the mounting plate of the plate with the pressing tip extending inward of a concave side of the mounting plate and the fingerpiece exposed externally of a convex side of the mounting plate so that the strap means can be fastened about a selected one of a user's foot and a user's leg with the pressure applying tip engaging a selected acupressure point and fingerpiece subsequently manually turned by a user to adjust the precise pressure applied by the tip while remaining in precise alignment with the acupressure point. The pair of edges of the plate at opposite ends of the arc remain stationary in contact with the body throughout tightening ensuring that the pressing tip remains on the acupressure point throughout the pressure adjustment.

Preferably, the mounting plate is molded in one piece of plastic in a rectangular shape with the longer side thereof being arcuate and the screw mounting means comprises an internally threaded land integrally formed on a convex side of the plate.

A device for applying pressure to selected acupresssure points on smaller toes comprises first and second, identical, elongate members each molded in one piece of plastic with respective opposite ends defining a pair of body gripping jaws and a pair of finger-pieces, respectively, each member having medially located pin and socket means which are intermatable when the members are engaged in side by side relation to provide a fulcrum; and, a resilient, force applying band encircling the members to form a clip.

As the members are of identical construction, only a single mold is required minimizing tooling and inventory costs.

A further clamping device for application to a big toe comprises a body molded in one piece of plastic and a tightening screw, the body comprising a toe stool formed by a blind ended socket having a pair of circumferentially spaced slots extending axially from an open end toward a blind end to define a screw mounting limb on one side and a toe-nail portion receiving trough on another other side, screw mounting means on the screw mounting limb. The tightening screw has a pressure applying end terminating in a small, spherical pressing tip and an opposite, adjustment end, having a fingerpiece, and the tightening screw being mounted by the screw mounting means with the pressing tip extending into the socket and the fingerpiece accessible to the user for pressure adjustment by the user while a user's toe is received in the socket with the pressing tip engaging a selected acupressure point.

The stool ensures that the clamp remains accurately located on the toe throughout tightening.

The various devices may be supplied together as a set together with a set of instructions or a video explaining their mode of application.

BRIEF DESCRIPTION OF THE DRAWINGS

Specific embodiments of the invention will now be described by way of example only and with reference to the accompanying drawings in which:

FIG. 1 is a perspective view of a first embodiment of clamp applied to a person's hand;

FIG. 2 is a side elevation of the clamp shown in FIG. 1;

FIG. 3 is a perspective view of a second embodiment of the invention applied to the sole of a person's foot;

DESCRIPTION OF PARTICULAR EMBODIMENTS

Figure 4:
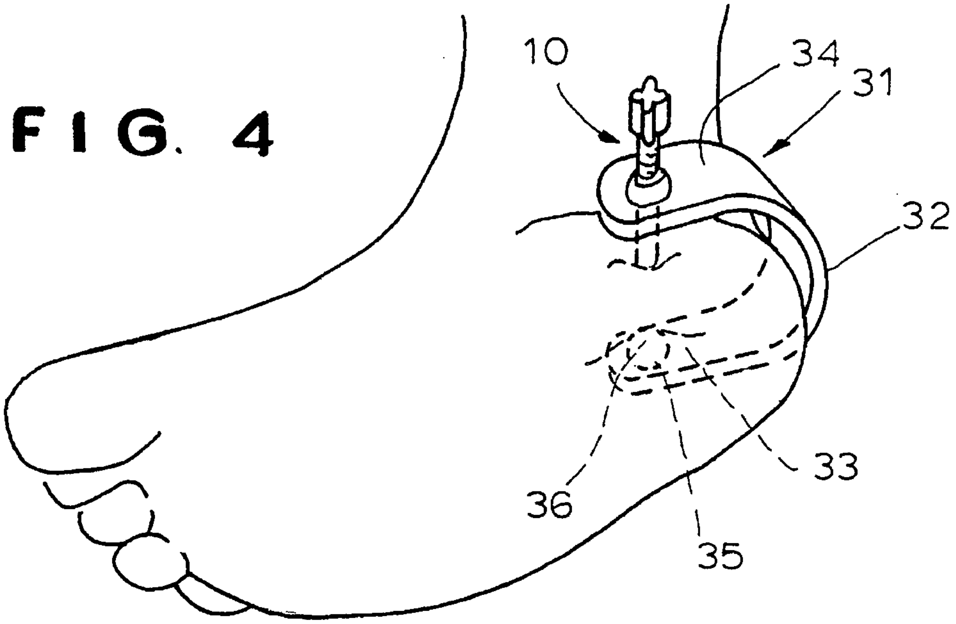
FIG. 4 is a perspective view of a third embodiment of clamping device applied to a person's foot adjacent the heel.

The first embodiment shown in FIGS. 1 and 2 comprises a substantially U-shape band 1 of uniform width and thickness throughout its length which is molded in one piece from high impact polystyrene to form an arcuate bridge or bight portion 2 interconnecting first and second, opposite, arm-like end portions 3 and 4, respectively. The first end portion 3 extends substantially perpendicularly of a central part or apex of the bridge 2 and has a counter-abutting protuberance or pimple 5 with a spherically domed, skin engaging, free end 6 integrally formed on an inner side thereof to protrude internally of the band.

The second end portion 4 is of slightly greater length than the first and extends at a small outward divergence of approximately 18 degrees from the perpendicular and has an outward protruding, spherical screw mounting land 7 formed on an outer side thereof. A threaded bore 8 is tapped completely through the mounting land 7 and the second end portion and receives a shank 9 of a tightening screw 10 having an inner pressure applying end 11 terminating in a small, spherical pressing tip 12 and an outer, adjustment end, formed with a fingerpiece 13.

Approximate dimensions in inches for the clamp are: span of the band, as measured between the inner surfaces of the tips of the free ends, approximately 3.5; band width 1.1; band thickness 0.25; protuberance 0.25; total length of tightening member 3.7. The diameter of the pressing tip of the screw is approximately 0.22 inches.

To facilitate separation from the mold a taper or draft angle of 1 degree may be formed form the center, (parting) line 13 of the band to opposite longitudinal edges which are all smoothly rounded or chamfered.

To apply the device, the pressing tip 12 of the screw is located on the acupuncture point known as Hoku which is located at the dorsum of the hand between the first and second metacarpal bone, near the radial side of the second metacarpal bone and the screw tightened to create a distinct but comfortable pressure. The counter-abutting protuberance 5 should then line up directly opposite the Hoku point and placed just below the outer hand bone as shown in FIG. 1.

As a result of the divergence of the second end portion 4, the line of action or screw axis is inclined at an acute angle to the central axis or line of action of the counter-abutting protuberance 5 for simultaneous application of pressures along non aligned axes to the two spaced apart locations.

This enables the pressing tip 12 to apply pressure obliquely of the surface of the skin hand into precise engagement with the acupressure point.

A second embodiment, shown in FIG. 3, for application to the foot or to the leg immediately below the knee, may comprise a rectangular mounting plate 21 of arcuate section formed at respective opposite longitudinal ends with strap anchoring slots 22, 22'. A pair of fastening straps 23,23' of complementary hook and loop form fastening fabric material such as VELCRO (Registered Trade Mark) are attached to the anchoring portions. A screw mounting land 24 is formed at the center of the convex face and a threaded bore extends completely through the land and plate and receives a shank of a tightening screw 25 of identical construction to that described above extends. The mounting plate has a projected length of 2.36 inches and a width of 1.5 inches with an inner surface radius of 2.06 inches and a substantially uniform thickness of 0.25 inches.

Fastening the strap means about a body part such as the foot enables the screw tip to be retained precisely aligned or engaging the selected acupressure point, substantially at the center of the underside of the foot, as shown, with the fingerpiece exposed for hand tightening by the user ensuring that a preferred appropriate pressure can be applied by the tip to the precise point of the body part while the opposite longitudinal arcuate ends of the mounting plate remain in stabilizing engagement with the surrounding tissue.

In an alternative application to the leg, the acupressure point is located by placing the tip of the right thumb along the outer shinbone of the right leg about 5 or 6 inches below the kneecap and the tip of the thumb is slowly slid upward along the shinbone until reaching a hollow indentation at a bone which protrudes from the shin bone at about two inches below the kneecap. The tip of the screw is located in the indentation and the straps fastened together underneath the calf muscle to hold the clamp in place. The screw is then manually tightened to obtain a distinct but comfortable pressure.

In Chinese acupuncture this location is a master pressure point enabling an immediately profound tranquilizing and tonic effect in a matter of minutes.

A third embodiment, shown in FIG. 4, for applying pressure to a portion of the foot adjacent the heel comprises a substantially U-shaped band 31 of uniform width and thickness throughout its length which is molded in one piece from high impact polystyrene to form an arcuate bridge portion or bight 32 interconnecting opposite, arm-like end portions 33 and 34, respectively which extend in substantially parallel relation. Both end portion 33 extends substantially perpendicularly of a central part or apex of the bridge. A counter-abutting protuberance or pimple 35 with a spherically domed, skin engaging, free end 36 integrally formed on an inner side of the first end portion 33 to protrude internally of the band and a tightening screw mounting land 37 having an internal bore 38 is formed at a precisely opposite location on an outer side of the other end portion 36. The tightening screw 10 is identical to those described above. The clamp band is essential stiff with slight interarm flexibility.

The correct pressure point is to be found at the mid point of an imaginary line drawn between the outer ankle bone and the furthest part of the heel. The protuberance should be aligned directly opposite the screw head, which is midway between the inner ankle bone and the furthest part of the heel.

Figure 5:
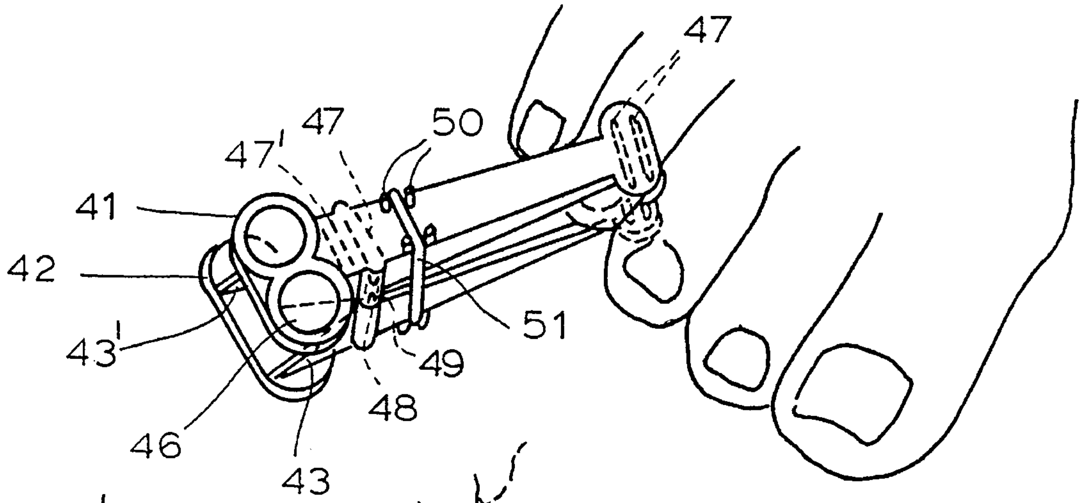
FIG. 5 is a perspective view of a third embodiment of applied to a smaller toe; and, FIG. 6 is a perspective view of a fourth embodiment of clamping device applied to a large toe.

As shown in FIG. 5, a clip for application to the smaller toes comprises first and second, identical, elongate members 41 and 42, respectively, each molded from high impact polystyrene into channel section with the channel walls 43,43' tapering from a medial portion (which is closer to one end) of maximum height, towards respective opposite ends which are formed with finger pieces 46 and pairs of transverse pressure applying ribs 47, respectively. A transverse strengthening wall 48 bridges each pair of channel walls at the medial portion and a pin 48 and a complementary socket 49 upstand at respective junctions thereof so that when the two members are aligned with channel mouths adjacent, the pin and socket on one member mate with the pin and socket on the other member permitting pivotal movement of the ends together and apart. Two pairs of locating posts 50 are molded on the channel base and a resilient retaining band 51 is trapped therebetween encircling both members.

Squeezing the finger pieces 41 and 42 together pivots the other ends apart to enable the ribs 47 to clamp onto a small toe at the location shown in the Figure, which is on the side adjacent the root end of the nail.

Figure 6:
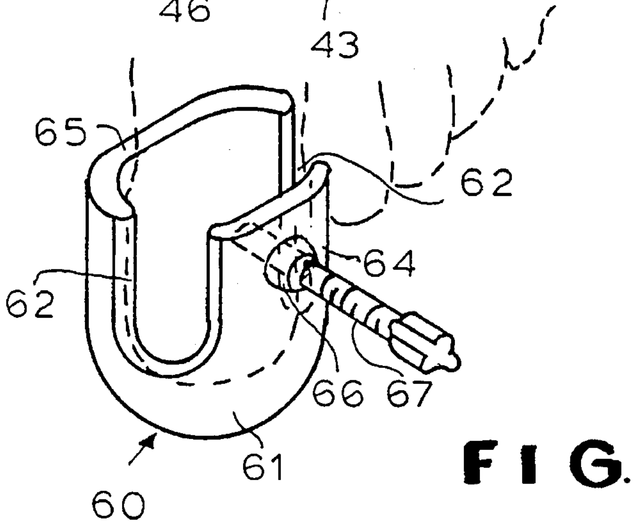

The embodiment shown in FIG. 6 is for application to the big toe and comprises a toe stool 60 formed by a generally oval, blind ended socket 61 having a pair of circumferentially spaced slots 62 extending axially on one side from an open, toe admitting end 63 to define a lower screw mounting limb 64 on one side and an upper toe-nail side receiving channel 65 on the other side. The limb 64 is integrally formed with a screw retaining land 66 retaining a screw-form tightening member 67, as in the prior embodiments.

The appropriate pressure point, known as the pituitary gland reflex, is location at the junction of lines extending from the center tip of the large toe to the base and across the widest part of the toe. The tip of the screw should be located on this point and the screw tightened as snugly as possible without causing much discomfort. Application to both large toes is preferred.

A treatment set contains two items of each embodiment thereby affording a complete range of self administered treatment for substantially all symptoms.

It will be apparent to the technician that as a result of the designs the devices can all be mass produced in high volume at low cost by molding from high impact polystyrene while an identically formed tightening member can be used with all versions further reducing tooling and inventory costs.

We claim:

1. A clamping device for the application of pressure to an acupressure point comprising:

a unitary, generally U-shape band having opposite end portions connected by a bight, screw mounting means on one end portion and an inward extending, counter-abutting protuberance having a spherical tip formed on an inner side of an opposite end portion; and, a tightening screw having a pressure applying end terminating in a smooth, spherical pressing tip substantially smaller than the protuberance and an opposite, adjustment end, having a fingerpiece, the tightening screw being mounted by said screw mounting means with the tip extending inward and the fingerpiece accessible outside the end portion, wherein, in stable, underformed condition of the clamping device, the end portions of the band are divergent for simultaneous application of pressures along non aligned axes at two spaced apart locations of a body part such as a back of a hand so that the clamping device can be mounted on a user's body part engaged between the protuberance and the pressing tip and the fingerpiece can be manually rotated by the user to adjust applied pressure while maintaining aligned engagement of the pressing tip with a selected acupressure point with the protuberance providing a stabilizing counterabutment.

2. A clamping device according to claim 1 wherein the band is molded in one piece from plastic.

3. A clamping device according to claim 2 wherein the screw mounting means is formed by a land integrally molded on an outside of the one end portion.

4. A clamping device for the application of pressure to a Hoku acupressure point comprising:

a unitary, generally U-shape band having opposite end portions connected by a bight having a mouth, screw mounting means on one end portion and a counterabutment formed on an inner side of an opposite end portion; and, a tightening screw having a pressure applying end terminating in a small, spherical pressing tip and an opposite, adjustment end, having a fingerpiece, the tightening screw being mounted by said screw mounting means with the tip extending inward, inclined to a line of action of the counterabutment away from the bight, in stable, undeformed condition of the clamping device and the fingerpiece accessible outside the end portion, so that the clamping device can be mounted on a user's hand with the pressing tip located on the Hoku point at the dorsum of the hand between the first and second metacarpal bone, adjacent a radial side of the second metacarpal bone and the counter-abutment aligned directly opposite the Hoku point engaging adjacent and below the outer hand bone and the pressing tip, and the fingerpiece can be manually rotated by the user to adjust applied pressure while maintaining aligned engagement of the pressing tip with the Hoku point with simultaneous application of pressures to the hand along non- aligned axes.

5. A clamping device according to claim 4 wherein the opposite end portion extends perpendicularly to a central portion of the bight.

6. A clamping device according to claim 5 wherein the counterabutment comprises a pimple-like protuberance having a smoothly rounded body engaging end substantially larger than the pressing tip and a central longitudinal axis intersecting the screw mounting means.

7. A clamping device according to claim 5 wherein the one end portion extends in divergent fashion away from the opposite end portion.

8. A clamping device according to claim 6 wherein the band is molded in one piece from plastic.

9. A clamping device according to claim 8 wherein the screw mounting means is formed by a land integrally molded on an outside of the one end portion.

10. A device for application to selected acupressure points on the sole of the foot and the leg, immediately below the knee, comprising a unitary mounting plate of arcuate section having opposite body engaging edges and formed at a central location with screw mounting means and with strap anchoring portions at opposite circumferential ends;

fastening strap means attached to the anchoring portions; and, a tightening screw having a pressure applying end terminating in a small, spherical pressing tip and an opposite, adjustment end, having a fingerpiece, the screw mounting means mounting the tightening screw extending through the center of the mounting plate with the pressing tip extending inward of a concave side of the mounting plate and the fingerpiece exposed externally of a convex side of the mounting plate so that the strap means can be fastened about a selected one of a user's foot and a user's leg with the pressure applying tip engaging a selected acupressure point and the opposite ends engaging adjacent body parts and the fingerpiece subsequently manually turned by a user to adjust the pressure applied by the tip while remaining in precise alignment with the acupressure point.

11. A device according to claim 13 wherein the mounting plate is molded in one piece of plastic in a rectangular shape with a longer side thereof arcuate and the screw mounting means comprises an internally threaded land integrally formed on the convex side of the mounting plate.

12. A device for applying pressure to selected acupresssure points on smaller toes comprising first and second, identical, elongate members each molded in one piece of plastic with respective opposite ends defining a pair of body gripping jaws and a pair of finger-pieces, respectively, each member having medially located pin and socket means which are intermatable when the members are engaged in side by side relation to provide a fulcrum; and, a resilient, force applying band encircling the members to form a clip.

13. A clamping device for application to a big toe comprises a body molded in one piece of plastic and a tightening screw, the body comprising a toe stool formed by a blind ended socket having a pair of circumferentially spaced slots extending axially from an open end toward a blind end to define a screw mounting limb on one side and a toe-nail portion receiving trough on another other side, screw mounting means on the screw mounting limb, the tightening screw having a pressure applying end terminating in a small, spherical pressing tip and an opposite, adjustment end, having a fingerpiece, and the tightening screw being mounted by the screw mounting means with the pressing tip extending into the socket and the fingerpiece accessible to the user for pressure adjustment by the user while a user's toe is received in the socket with the pressing tip engaging a selected acupressure point.

* * * * *